United States Patent [19]

Narayanan et al.

[11] Patent Number: 5,603,942
[45] Date of Patent: Feb. 18, 1997

[54] STABLE, SINGLE PHASE W/O MICROEMULSION MATRIX FORMULATION FOR FORMING SPRAYABLE, AEROSOL AGRICULTURALLY ACTIVE COMPOSITIONS

[75] Inventors: Kolazi S. Narayanan; Milla Kaminsky, both of Wayne; Robert M. Ianniello, Oak Ridge, all of N.J.

[73] Assignee: ISP Investments Inc., Wilmington, Del.

[21] Appl. No.: 444,600

[22] Filed: May 19, 1995

[51] Int. Cl.$^6$ ............................................. A01N 25/30
[52] U.S. Cl. .................................. 424/405; 424/45
[58] Field of Search ........................... 424/405, 45

[56] References Cited

U.S. PATENT DOCUMENTS

| | | | |
|---|---|---|---|
| 4,536,323 | 8/1985 | Stopper | 252/305 |
| 5,283,229 | 2/1994 | Narayanan et al. | 504/116 |
| 5,354,726 | 10/1994 | Narayanan et al. | 504/116 |
| 5,466,458 | 11/1995 | Martin et al. | 424/405 |

*Primary Examiner*—Amy Hulina
*Attorney, Agent, or Firm*—Walter Katz; Marilyn J. Maue; Joshua J. Ward

[57] ABSTRACT

Stable, single phase w/o aerosol microemulsion final use compositions containing a sprayable agriculturally active composition are described herein.

14 Claims, No Drawings

STABLE, SINGLE PHASE W/O MICROEMULSION MATRIX FORMULATION FOR FORMING SPRAYABLE, AEROSOL AGRICULTURALLY ACTIVE COMPOSITIONS

BACKGROUND OF THE INVENTION

1. Field of the Invention

This invention relates to microemulsion compositions, and, more particularly, to stable, single phase w/o microemulsion matrix formulations for forming sprayable aerosol agriculturally active compositions.

2. Description of the Prior Art

Microemulsion compositions are known in the art for delivering agriculturally active ingredients to a desired site. Such compositions usually are pump sprayed onto the target location. However, for a more rapid, 100% knockdown (kill) rate for insecticides it is desired to provide an aerosol system of a water-based formulation which accommodates a maximized quantity of water in an w/o microemulsion matrix.

SUMMARY AND DETAILED DESCRIPTION OF THE INVENTION

In accordance with the invention, a water-based, w/o microemulsion matrix, is provided herein which can accommodate an agriculturally active ingredient and an aerosol propellant as stable, single phase systems for delivery of spray particles of the active ingredient to an insect-infected site. These compositions are effective in producing a 100% kill at a substantially instantaneous knockdown rate. The microemulsion formulations can accommodate large amounts of water and the agriculturally active ingredient (insecticides), and a desirable amount of propellant loading, all within a stable, single phase microemulsion having predetermined amounts of oil, emulsifier and cosolvent/cosurfactant components.

The liquid microemulsion matrix of the invention (without agriculturally active ingredient and propellant) can be formulated as desired with a particular active ingredient for final use, e.g. an insecticide, such as D-allethrin, D-phenethrin, and the like; a herbicide, a fungicide, or any useful agricultural chemical.

In particular, the stable, sprayable w/o single phase microemulsion of the invention can deliver aerosol particles of about ≦0.05 microns containing an insecticide which is capable of 100% kill (knockdown) of target insects within 5 minutes.

The matrix formulations and final use compositions of the invention are described below.

TABLE 1

| | | Weight % | |
|---|---|---|---|
| | Component | Suitable | Preferred |
| (a) | Oil long chain ($C_8$–$C_{18}$) hydrocarbon e.g. dodecane | 2–20 | 5–10 |
| (b) | Water | 20–50 | 25–30 |
| (c) | Propellant e.g. $C_3$–$C_4$ mixed hydrocarbon, A-46 | 20–45 | 25–40 |
| (d) | Emulsifier e.g. nonylphenyl ethoxylate with 5–12 EOs, preferably 6–10 EOs and, most preferably, 9–10 EOs, such as Igepal® CO-520, CO-630, CO-660 and CO-730 | 10–25 | 12–20 |
| (e) | Cosolvent/Coemulsifier e.g. long chain ($C_8$–$C_{18}$) alkyl pyrrolidone, preferably octylpyrrolidone (Agsol® Ex 8); and/or pentanol | 15–35 | 20–30 |
| (f) | Agriculturally Active Ingredient e.g. insecticide, such as D-allethrin or D-phenethrin | 0.01–5 | 0.05–2 |

A matrix composition not containing the propellant is described below.

TABLE 2

| | | Weight % | |
|---|---|---|---|
| | Component | Suitable | Preferred |
| (a) | Oil | 3–25 | 5–15 |
| (b) | Water | 25–45 | 30–40 |
| (d) | Emulsifier | 13–25 | 15–22 |
| (e) | Cosolvent/Coemulsifier | 18–40 | 20–30 |

A matrix composition not containing the propellant, however, with an agriculturally active ingredient is shown in Table 3.

TABLE 3

| Formulation of Table 2 | Suitable | Preferred |
|---|---|---|
| (f) Agriculturally Active Ingredient | 0.015–6 | 0.06–2.5 |

A matrix composition with propellant is described below in Table 4.

TABLE 4

| | | Weight % | |
|---|---|---|---|
| | Component | Suitable | Preferred |
| (a) | Oil | 2–20 | 5–10 |
| (b) | Water | 25–50 | 25–30 |
| (c) | Propellant | 20–45 | 25–40 |
| (d) | Emulsifier | 10–25 | 12–20 |
| (e) | Cosolvent/Coemulsifier | 15–35 | 20–30 |

These single phase, water-based microemulsion matrix and use compositions can be stored at 5° C. as a single phase system, and at 45° C., without phase separation. Furthermore, even after centrifugation at 3000 rpm for 30 minutes, there is no evidence of phase separation of the microemulsion.

If desired, UV-protecting monomers, oligomers and oils can be loaded into the matrix and final use compositions to provide UV protection for those agriculturally active ingredients which are sensitive to sunlight.

EXAMPLES

TABLE 5

| Ingredients | EXAMPLE NO. 1 | 2 | 3 | 4 | 5 |
|---|---|---|---|---|---|
| Dodecane | 10 | 12 | 14 | 6 | 15 |
| Igepal ® CO-520 | — | — | — | — | 18 |
| Igepal ® CO-630 | 20 | — | — | — | — |
| Igepal ® CO-660 | — | 11 | 21 | 27 | — |
| Igepal ® CO-730 | — | 9 | — | — | — |
| Gafac ® RE-610 | — | — | — | — | 2 |
| Agsol ® Ex-8 | 36 | 13 | 8 | 0 | 15 |
| Pentanol | — | 20 | 11 | 27 | 11 |
| Glycerol | — | — | 10 | — | — |
| Water | 34 | 35 | 36 | 40 | 50 |

TABLE 6

| RESULTS | EXAMPLE NO. 1 | 2 | 3 | 4 | 5 |
|---|---|---|---|---|---|
| Appearance at RT | clear | clear | clear | clear | clear |
| Appearance at 40–45° C. | clear | clear | cloudy | clear | cloudy |
| Propellant loading capacity | ≧35% | 35% | >25% | ≦25% | 25% |
| Appearance after propellant loading at room temperature | clear | clear | clear | clear | clear |
| Appearance at 45° C. with propellant | clear | clear | clear | clear | — |

What is claimed is:

1. A stable single phase w/o aerosol microemulsion matrix for making a sprayable agriculturally active composition, consisting essentially of, by weight, (a) 2–20% of a $C_8$-$C_{18}$ hydrocarbon, (b) 25–50% of water, (c) 20–45% of a propellant, (d) 10–20% of an emulsifier, and (e) 15–35% of a cosolvent/coemulsifier which is a $C_8$-$C_{18}$ alkyl pyrrolidone or pentanol, or mixtures thereof.

2. A matrix according to claim 1 wherein (a) is 5–10%, (b) is 30–40%, (c) is 25–40%, (d) is 12–18%, and (e) is 30–40%.

3. A matrix according to claim 1 wherein (a) is a $C_{12}$ hydrocarbon, and (d) is a nonylphenyl ethoxylate with 5–12 EOs.

4. A matrix according to claim 1 wherein (c) is a $C_3$-$C_4$ mixed hydrocarbon.

5. A matrix according to claim 1 wherein (d) is a nonylphenyl ethoxylate with 6–10 EOs.

6. A matrix according to claim 1 wherein (a) is 10% dodecane, (b) is 34%, (c) is 30%, (d) is 20% and (e) is 35%.

7. A stable single phase w/o aerosol microemulsion composition comprising the matrix formulation of claim 1 and (f) 0.01–5% by weight of an agriculturally active ingredient.

8. A composition according to claim 7 wherein (f) is an insecticide.

9. A composition according to claim 7 including 0.05–2% of (f).

10. A composition according to claim 7 wherein (f) is a pyrethroid.

11. A composition according to claim 7 wherein (f) is D-allethrin or D-phenethrin, or mixtures thereof.

12. A stable, single phase w/o microemulsion matrix for making a sprayable agriculturally active composition, consisting essentially of, by weight, (a) 3–25% of a $C_8$-$C_{18}$ hydrocarbon, (b) 25–45% of water, (d) 13–25% of an emulsifier, (e) 18–40% of a cosolvent/coemulsifier which is a $C_8$-$C_{18}$ alkyl pyrrolidone or pentanol, or mixtures thereof.

13. A matrix according to claim 12 wherein (a) is 10–15%, (b) is 30–35%, (d) is 15–22%, and (e) is 20–25%.

14. A matrix according to claim 12 wherein (a) is a $C_{12}$ hydrocarbon, and (d) is a nonylphenyl ethoxylate with 5–10 EOs.

* * * * *